(12) United States Patent
Hsu et al.

(10) Patent No.: US 8,241,608 B2
(45) Date of Patent: Aug. 14, 2012

(54) **TREATING ALLERGY WITH DETOXIFIED *E. COLI* HEAT-LABILE ENTEROTOXIN**

(75) Inventors: Yu-Shen Hsu, Xizhi (TW); Jiu-Yao Wang, Tainan (TW)

(73) Assignees: Development Center for Biotechnology, Taipei (TW); DCB-USA LLC, Wilmington, DE (US)

( * ) Notice: Subject to any disclaimer, the term of this patent is extended or adjusted under 35 U.S.C. 154(b) by 95 days.

(21) Appl. No.: 12/729,649

(22) Filed: Mar. 23, 2010

(65) Prior Publication Data

US 2011/0236424 A1    Sep. 29, 2011

(51) Int. Cl.
*A61K 49/00* (2006.01)
*A61K 39/02* (2006.01)
*A61K 39/00* (2006.01)

(52) U.S. Cl. .... 424/9.2; 424/9.1; 424/185.1; 424/234.1; 424/236.1; 424/241.1; 530/300; 530/350

(58) Field of Classification Search ................... 424/9.1, 424/9.2, 185.1, 234.1, 236.1, 241.1; 530/300, 530/350
See application file for complete search history.

(56) References Cited

U.S. PATENT DOCUMENTS

| | | | |
|---|---|---|---|
| 6,033,673 A | 3/2000 | Clements | |
| 7,208,155 B1 | 4/2007 | Williams et al. | |
| 2003/0113338 A1 | 6/2003 | Pizza et al. | |
| 2008/0102078 A1* | 5/2008 | Hsu et al. | 424/189.1 |
| 2008/0206284 A1 | 8/2008 | Williams et al. | |

OTHER PUBLICATIONS

Pizza et al. Mucosal Vaccines; Non Toxic Derivatives of LT and CT as Mucosal Adjuvants: Vaccine. 19:2534-2541 (2001).

* cited by examiner

*Primary Examiner* — Rodney P. Swartz
(74) *Attorney, Agent, or Firm* — Occhiuti Rohlicek & Tsao LLP

(57) ABSTRACT

A method for treating allergy with a pharmaceutical composition containing a detoxified *E. coli* heat-labile enterotoxin, and, optionally, an allergen.

12 Claims, 9 Drawing Sheets

Fig. 1

Preventive protocol:

Therapeutic protocol:

↑ : intranasal treatment with (a) normal saline (10 μl); (b) Der p (20 μg); (c) LT(S61K) (10 μg); or (d) LT(S61K)/Der p (10 μg/20 μg)

↑ : sensitization and boost by intradermal injection of 40 μg Der p/IFA

↑ : intratracheal airway challenge with 50 μg Der p

↑ : analyzing airway hyper-responsiveness x : sacrificed

B. TNF-α

D. Eotaxin

E. TARC

(a) Serum

Fig. 4(Cont'd)

(b) BAL fluid

Fig. 5

(a) Serum

Fig. 5 (Cont'd)

(b) BAL fluid

TREATING ALLERGY WITH DETOXIFIED E. COLI HEAT-LABILE ENTEROTOXIN

BACKGROUND OF THE INVENTION

Allergic asthma, mediated by pathologic Th2-type immune responses, is a major healthy problem in western countries. Symptoms of allergic asthma include increased mucus production and airway hyper-responsiveness. Repetitive exposure to allergens is an important contributing factor to this disease.

Steroids and other anti-inflammatory drugs are commonly used for treating allergic asthma. These drugs only alleviate asthma syndromes and do not prevent occurrence of allergic immune responses. Recently, allergy vaccine was developed as a preventive approach. A typical allergy vaccine contains an allergen (e.g., a pollen allergen or a microbial allergen) to induce specific immune responses and an adjuvant (e.g., CpG oligonucleotide or a mutated E. coli heat-labile enterotoxin) to enhance the allergen-specific immune responses.

SUMMARY OF THE INVENTION

The present invention is based on an unexpected discovery that a detoxified E. coli heat-labile enterotoxin (LT) mutant, either alone or in combination with an allergen, is effective in treating allergic asthma.

Accordingly, one aspect of this invention features a method for treating allergy (e.g., allergic asthma) by administering to a subject in need thereof (e.g., a human suffering from or at risk for allergy) a detoxified LT mutant in an amount effective for inducing an anti-allergic response. The detoxified LT mutant exhibits substantially reduced toxicity as compared to its wild-type counterpart. Namely, its toxicity level does not exceed 1% of that of its wild-type LT counterpart when determined in the conventional Y-1 adrenal cell assay or does not exceed 10% of that of the wild-type counterpart when determined in the conventional Caco-2 cell assay.

The detoxified LT used in the method of this invention can contain a mutated subunit A, e.g., a subunit A mutant including an amino acid substitution at the position corresponding to position 61 or position 63 in SEQ ID NO:1 shown below. LTS61K and LTS63K are two examples. The detoxified LT, alone or combined with an allergen, can be formulated in a pharmaceutical composition to be administered mucosally (e.g., intranasally or sublingually) or by other routes (e.g., transcutaneous delivery).

Also within the scope of this invention is the pharmaceutical composition mentioned above for use in treating allergy by, e.g., mucosal or transcutaneous administration, or for use in manufacturing a medicament for the treatment.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The drawings are first described.

DETAILED DESCRIPTION OF THE INVENTION

Described herein is a method for treating allergy (e.g., allergic asthma) with an effective amount of a detoxified LT mutant, either taken alone or in combination with an allergen. The term "treating" as used herein refers to the application or administration of a composition including one or more active agents to a subject, who has an allergic disease, a symptom of the allergic disease, or a predisposition toward the allergic disease, with the purpose to cure, heal, alleviate, relieve, alter, remedy, ameliorate, improve, or affect the disease, the symptoms of the disease, or the predisposition toward the disease. "An effective amount" of the detoxified LT mutant used in the method of this invention refers to the amount of the LT mutant required to confer therapeutic effects on a subject, i.e., inducing an anti-allergic response, thereby alleviating allergic symptoms in the subject. Anti-allergic responses include inhibiting infiltration and recruitment of activated immune cells associated with allergic responses, enhancing secretion of IgA (particularly non-antigen specific IgA), reducing TARC secretion, and suppressing Th2-type immune responses. Th2-type immune responses are characterized by the release of Th2-type cytokines (e.g., IL-4, IL-5, IL-10, and IL-13), leading to generation of humoral immunity, activation of espinophil, regulation of cell-mediated immune response, and stimulation of IgE production. Effective amounts vary, as recognized by those skilled in the art, depending on route of administration, excipient usage, and co-usage with other active agents.

A detoxified LT mutant suitable for use in the method of this invention exhibits substantially reduced cytotoxicity relative to its wild-type counterpart, as determined in either the Y-1 adrenal cell assay or the Caco-2 cell assay, both of which are well known in the art. See, e.g., David et al., 1975, Infection and Immunity, 11:334-336; Cheng et al., 1999, Vaccine 18:38-49; Grant, C. C. et al., 1994, *Infection and immunity*, 62:4270-4278; Cheng, E. et al, 2000, *Vaccine*, 18:38-49; and Park, E. J. et al., 1999, *Experimental and molecular medicine*, 31:101-107. Below are brief descriptions of these two assays.

To perform the Y-1 adrenal cell assay, mouse Y-1 adrenal tumor cells (ATCC CCL-79), preferably maintained in Ham's F12 media supplemented with 15% horse serum, 2.5% fetal bovine serum, 2 mM L-glutamine, and 1.5 g/L sodium bicarbonate, can be seeded in 96-well flat-bottom plates at a concentration of $2\times10^4$ cells per well (200 ul/well) at 37° C. in 5% CO2 for 48 hrs. The cells are washed several times with 1×PBS (pH 7.4) and then treated with a test LT (either wild-type LT or mutated LT) at various concentrations under 37° C. with 5% CO2 supply. Around 24 hours after the treatment, the cells can be observed under a light microscope to examine occurrence of cell rounding. The toxicity of the LT in the test sample is defined as the minimum LT concentration required to initiate cell rounding (ECi) or the LT concentration required for inducing 50% cell rounding ($EC_{50}$).

The Caco-2 cell assay can be performed as follows. Caco-2 cells (ATCC HTB-37) are maintained in MEM-α medium supplemented with 20% FBS in a 24-well plate at a concentration of $5\times10^4$ cells per well. When the cells are close to 100% confluency, the culture medium is replaced with MEM-α supplemented with 1% FBS and 1 mM 3-isobutyl-1-methylxanthine (IBMX). After being incubated for 30 min with 5% $CO_2$ supply, the cells are mixed with a test LT and incubated for 4 hours. The cells are washed several times with cold PBS, mixed with 200 μl of 0.1 N HCl for 15 minutes at room temperature, and then lyzed, the supernatants collected. The levels of the cAMP in the supernatants, representing the toxicity level of the test LT, are determined by ELISA using, e.g., the kit provided by Assay designs; Correlate-EIA.

The detoxified LT mutant can be prepared by introducing one or more mutations into a wild-type LT, either in its subunit A or in its subunit B, via conventional genetic engineering technology. Shown below are the amino acid sequences of a wild-type subunit A (mature form) and a wild-type subunit B, and a nucleotide sequence encoding both the A and B subunits.

```
Amino acid sequence (SEQ ID NO: 1) of mature LT_A
NGDKLYRADS RPPDEIKRSG GLMPRGHNEY FDRGTQMNIN LYDHARGTQT GFVRYDDGYV    60

STSLSLRSAH LAGQSILSGY STYYIYVIAT APNMFNVNDV LGVYSPHPYE QEVSALGGIP   120

YSQIYGWYRV NFGVIDERLH RNREYRDRYY RNLNIAPAED GYRLAGFPPD HQAWREEPWI   180

HHAPQGCGNS SRTITGDTCN EETQNLSTIY LRKYQSKVKR QIFSDYQSEV DIYNRIRNEL   240

Amino acid sequence (SEQ ID NO: 2) of LT_B
MNKVKCYVLF TALLSSLCAY GAPQSITELC SEYRNTQIYT INDKILSYTE SMAGKREMVI    60

ITFKSGATFQ VEVPGSQHID SQKKAIERMK DTLRITYLTE TKIDKLCVWN NKTPNSIAAI   120

SMEN

Nucleotide sequence (SEQ ID NO: 3) of LT
(Subunit A: 1-777; Subunit B: 774-1148)
atgaaaaata taactttcat ttttttatt ttattagcat cgccattata tgcaaatggc     60
gacaaattat accgtgctga ctctagaccc ccagatgaaa taaaacgttc cggaggtctt   120
atgcccagag ggcataatga gtacttcgat agaggaactc aaatgaatat taatctttat   180
gatcacgcga gaggaacaca aaccggcttt gtcagatatg atgacggata tgtttccact   240
tctcttagtt tgagaagtgc tcacttagca ggacagtcta tattatcagg atattccact   300
tactatatat atgttatagc gacagcacca aatatgttta atgttaatga tgtattaggc   360
gtatacagcc ctcacccata tgaacaggag gtttctgcgt taggtggaat accatattct   420
cagatatatg gatggtatcg tgttaatttt ggtgtgattg atgaacgatt acatcgtaac   480
agggaatata gagaccggta ttacagaaat ctgaatatag ctccggcaga ggatggttac   540
agattagcag gtttcccacc ggatcaccaa gcttggagag aagaaccctg gattcatcat   600
gcaccacaag gttgtggaaa ttcatcaaga acaattacag gtgatacttg taatgaggag   660
acccagaatc tgagcacaat atatctcagg aaatatcaat caaaagttaa gaggcagata   720
ttttcagact atcagtcaga ggttgacata tataacagaa ttcggaatga attatgaata   780
aagtaaaatg ttatgtttta tttacggcgt tactatcctc tctatgtgca tacggagctc   840
cccagtctat tacagaacta tgttcggaat atcgcaacac acaaatatat acgataaatg   900
acaagatact atcatatacg gaatcgatgg caggcaaaag agaaatggtt atcattacat   960
ttaagagcgg cgcaacattt caggtcgaag tcccgggcag tcaacatata gactcccaaa  1020 aaaagccat tgaaaggatg aaggacacat taagaatcac atatctgacc gagaccaaaa   1080
ttgataaatt atgtgtatgg aataataaaa cccccaattc aattgcggca atcagtatgg  1140 aaaactag
```

Preferably, the detoxified LT mutant contains a mutated A subunit that includes a mutated residue at a position essential to its ADP-ribosyltransferase activity, e.g., position 53, 61, 63, 69, 97, 104, 106, 110, or 112 in SEQ ID NO:1. See U.S. Pat. No. 6,149,919, US 20081012078, Cieplak et al., J. Biol. Chem. 270(51):30545-30550, 1995; and Cheng et al., Vaccine 18:38-49, 2000. In the LT mutant, the A and B subunits form the typical $AB_5$ holotoxin structure. In one example, the detoxified LT mutant (LTS61K) contains a mutated subunit A that includes K at position 61 in SEQ ID NO:1 and a wild-type subunit B. In another example, the detoxified LT mutant (LTS63K) contains a mutated subunit A that includes K at position 63 in SEQ ID NO:1 and a wild-type subunit B.

Other detoxified LT mutants are disclosed in US2001/0044416, Nawar et al., Infection and Immunity 73(3):1330-1342 (2005), Komase et al., Vaccine 16(2):248-254, 1993; Magagnoli et al., Infection and Immunity 64(12):5434-5438, 1996; WO99/47164, and U.S. Pat. No. 6,818,222.

A detoxified LT mutant can be prepared via conventional recombinant technology. For example, nucleotide sequences coding for both the A and B subunits of an LT mutant can be inserted into an expression cassette and expressed in a host cell (e.g., an *E. coli* cell). The A and B subunits can be self-resembled in the host cell to form a holotoxin, which can be isolated from the host cell via, e.g., chromatography. See US20081012078. The toxicity of the LT mutant thus prepared can be determined in either the Y-1 adrenal cell assay or the Caco-2 cell assay, both described above and those displaying substantially reduced toxicity are identified for use in the method of this invention.

Any of the detoxified LT mutants, either alone or in combination with one or more allergens, can be used for treating allergy. An allergen is a substance capable of inducing allergic reactions, i.e., immune reactions mediated by IgE, in a subject (e.g., a human) who has been repeatedly exposed to it. It can be any naturally occurring proteins, including pollen allergens (tree-, herb, weed-, and grass pollen allergens), insect allergens (inhalant, saliva and venom allergens, such as mite allergens, cockroach and midges allergens, and hymenopthera venom allergens), animal hair and dandruff allergens (from e.g. dog, cat, horse, rat, mouse etc.), and food allergens. Important pollen allergens from trees, grasses and herbs are such originating from the taxonomic orders of Fagales, Oleales, Pinales and platanaceae including birch (Betula), alder (Alnus), hazel (Corylus), hornbeam (Carpinus) and olive (Olea), cedar (Cryptomeriaand *Juniperus*), Plane tree (Platanus), the order of Poales including grasses of the genera *Lolium, Phleum, Poa, Cynodon, Dactylis, Holcus, Phalaris, Secale,* and *Sorghum*, the orders of Asterales and Urticales including herbs of the genera *Ambrosia, Artemisia,* and *Parietaria*. Other important inhalation allergens are those from house dust mites of the genus *Dermatophagoides* and *Euroglyphus*, storage mite e.g *Lepidoglyphys, Glycyphagus* and *Tyrophagus*, those from cockroaches, midges and fleas e.g. *Blatella, Periplaneta, Chironomus* and *Ctenoceppha-lides*, and those from mammals such as cat, dog and horse, venom allergens including such originating from stinging or biting insects such as those from the taxonomic order of Hymenoptera including bees (superfamily Apidae), wasps (superfamily Vespidea), and ants (superfamily Formicoidae). Important inhalation allergens from fungi are i.a. such originating from the genera *Alternaria* and *Cladosporium*. Examples of allergen for use in the method of this invention include, but are not limited to, house dust mite allergens, grass pollens, tree pollens, and food allergens. The allergen used in this invention can be a purified protein prepared by a conventional method. Alternative, it can be an extract prepared from a natural source of a desired allergen. Typically, an allergen extract contains one or more isoforms of the allergen. The allergen used in this invention can be a purified protein prepared by a conventional method. Alternative, it can be an extract prepared from a natural source of a desired allergen. Typically, an allergen extract contains one or more isoforms of the allergen.

Either the detoxified LT mutant or a combination of the LT mutant and one or more allergens can be formulated in a pharmaceutical composition (e.g., a vaccine), which can further contain a pharmaceutically acceptable carrier such as phosphate buffered saline or a bicarbonate solution. The carrier must be "acceptable" in the sense that it is compatible with the active ingredient of the composition, and preferably, capable of stabilizing the active ingredient and not deleterious to the subject to be treated. The carrier is selected on the basis of the mode and route of administration, and standard pharmaceutical practice. Suitable pharmaceutical carriers and diluents, as well as pharmaceutical necessities for their use, are described in Remington's Pharmaceutical Sciences.

Methods for preparing vaccines are generally well known in the art, as exemplified by U.S. Pat. Nos. 4,601,903; 4,599,231; 4,599,230; and 4,596,792. Vaccines may be prepared as injectables, as liquid solutions or emulsions. The LT mutant descried herein or its combination with an allergen may be mixed with physiologically acceptable excipients, which may include, water, saline, dextrose, glycerol, ethanol, and combinations thereof. The vaccine may further contain minor amounts of auxiliary substances such as wetting or emulsifying agents, or pH buffering agents to enhance the effectiveness of the vaccines. Vaccines may be administered parenterally (e.g., subcutaneous or intramuscular injection, or transcutaneous delivery) or mucosally (e.g., intranasally, sublingually, or orally). Alternatively, other modes of administration including suppositories, oral, or topical formulations may be desirable. For suppositories, binders and carriers may include, for example, polyalkalene glycols or triglycerides. Oral formulations may include normally employed incipients such as, for example, pharmaceutical grades of saccharine, cellulose, magnesium carbonate and the like. These compositions take the form of solutions, suspensions, tablets, pills, capsules, sustained release formulations or powders.

The vaccine is administered in a manner compatible with the dosage formulation, and in an amount that is therapeutically effective, protective, and immunogenic. Particularly, the amount of the detoxified LT mutant in the vaccine must be sufficient for reducing Th2-type immune responses. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the polypeptide of this invention. Suitable regimes for initial administration and booster doses are also variable, but may include an initial administration followed by subsequent administrations. The dosage of the vaccine may also depend on the route of administration and varies according to the size of the host.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

Example 1

Suppression of Th2-Type Immune Responses in Asthma Mice by LTS61K Alone or in Combination with Der p Allergen Female BALB/c mice (6~8 weeks) were used in this study. These mice were under specific-pathogen free and standard food/water conditions. The mice were treated following the preventive or therapeutic protocol shown in FIG. 1.

Preventive Protocol

Mice were randomly assigned into four groups, each treated with (i) saline (10 µl per mice), (ii) *Dermatophagoides pteronyssinus* (Der p from Allergon, 20 µg per mice), (iii) LT(S61K) (10 µg per mice), or (iv) LT(S61K) (10 µg) mixed with Der p (20 µg), per mouse on Day 0, Day 7, and Day 14. Two weeks later, the mice were sensitized with Der p twice (on Day 28 and Day 35) and then subjected to airway challenge on Day 42. They were sacrificed three days later.

Figure 2:
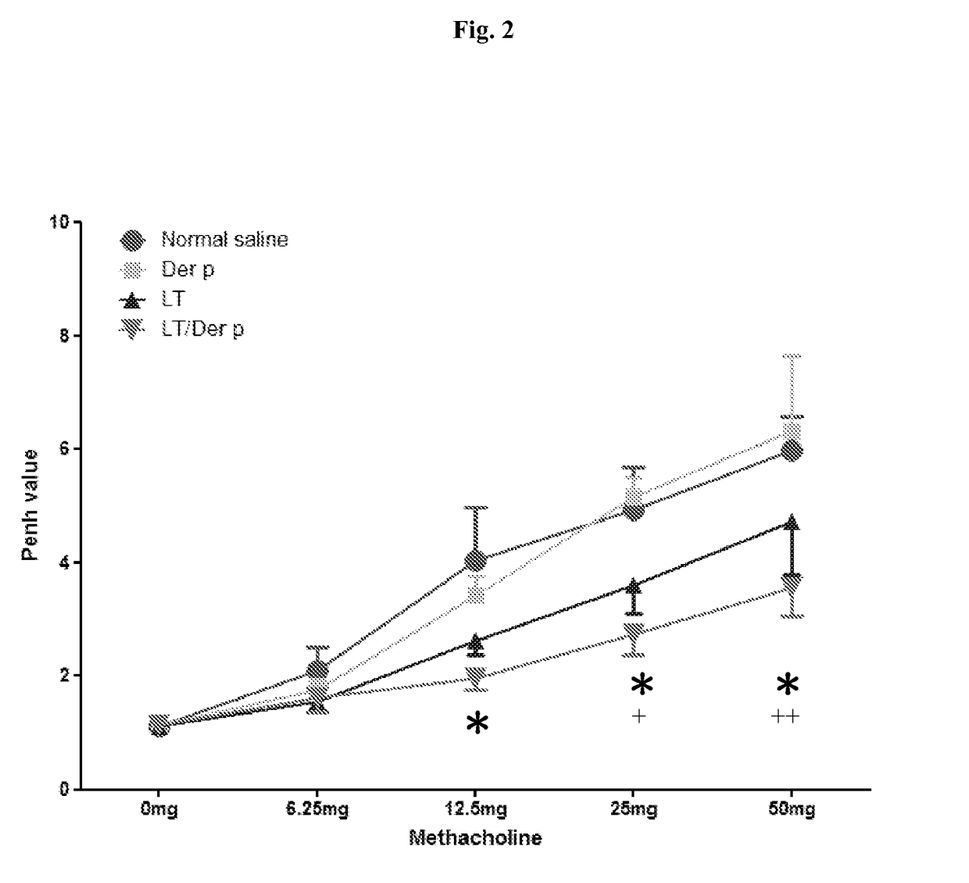
FIG. 2 is a chart showing levels of airway hyperresponsiveness (AHR) represented by enhanced pause (Penh) values in mice treated with LTS61K, Der p, or a combination thereof (LTS61K/Der p) following the preventive protocol shown in FIG. 1. *: $p<0.05$ (LTS61K/Der p versus normal saline). +: $p<0.05$ (LTS61K/Der p versus Der p alone). ++: $P<0.01$ (LTS61K/Der p versus Der p alone). The p values were obtained by two-way ANOVA. LT represents LTS61K.

The mice thus treated were examined to determine their AHR levels. More specifically, Penh values, representing dynamic airway resistance, were measured in those mice treated with various concentrations of acetyl-β-methylcholine chloride (methacholine) (Sigma-Aldrich) by Unrestrained Whole Body Plethysmography (Buxco) before sacrifice. As shown in FIG. 2, the mice treated with either LTS61K or the combination of LTS61K and Der p exhibited lower Penh values than those treated with saline and Der p. This result indicates that LTS61K, either alone or in combination with allergen Der p, reduced AHR in asthma mice.

Bronchoalveolar lavage (BAL) fluids were collected from the mice. The total cell numbers in the BAL fluids were counted after trypan blue staining. The results thus obtained indicate that less cells were present in the BAL fluids from the mice treated with LTS61K and LTS61K/Der p than in the BAL fluids from the mice treated with saline and Der p.

The levels of certain cytokines, e.g., IL-2, IL-5, TNF-a, eotasin, and TARC, in the BAL fluids were determined by sandwich ELISA, using analysis kits from e-Bioscience and R&D DuoSet. No difference in Th1-type cytokines, such as IL-2, was detected between the mice treated with LTS61K or LTS61K/Der p and the mice treated with saline or Der p. On the other hand, the levels of Th2-type cytokines, i.e., IL-5, eotaxin, and TARC, were lower in LTS61K- or LTS61K/Der p-treated mice than in saline or Der p-treated mice.

Further, splenocytes were isolated from the treated mice and cultured in 24-wells plates at a density of $1 \times 10^6$ cells/well in cRPMI supplemented with 10% (v/v) FBS, 1 mM sodium pyruvate, 50 mM 2-mecaptoethanol, 2 mM L-glutamine, 1 mM non-essential amino acid, 100 U/ml penicillin and 100 µg/ml streptomycin. The splenocytes were then challenged with 10 µg Der p for 2 to 3 days and the Supernatants were then collected. The levels of IFN-γ, IL-4, and IL-10 in the supernatants were determined using sandwich ELISA kits provided by R&D DuoSet. In addition, $1 \times 10^5$ splenocytes were seeded in a well of a 96-wells plate in the presence of 1 µg Der p and 0.1 µg or 1 µg PHA-L (Sigma-Aldrich). Cell proliferation was examined using a CCK-8 kit (Dojindo) 48 or 72 hour later. While no difference in splenocyte proliferation was observed among the four groups of mice, a lower level of both Th1 and Th2 cytokines was observed in the mice treated with LT(S61K) or LT(S61K)/Der p as relative to that in the mice treated with saline.

Taken together, the results discussed above show that LTS61K, either alone or in combination with Der p, suppressed TARC and Th2-type immune response when administered to asthma mice following the preventive protocol.

Therapeutic Protocol

Mice were first sensitized with Der p, which was mixed with incomplete Freund's adjuvant (IFA, Sigma-Aldrich) in equal volume, as follows. Each mouse was injected intra-dermally with 40 µg Der p on day 0 and day 7 and injected intra-tracheally with 50 µg Der p under light anesthesia by Zoletil 50 plus Rompun on day 14. The sensitized mice were randomly assigned into four groups, each administered intra-nasally with (i) saline (10 µl per mice), (ii) Der p (20 µg per mice), (iii) LT(S61K) (10 µg per mice), and (iv) LT(S61K) (10 µg) mixed with Der p (20 µg), per mouse under light anesthesia 3 times on Days 16, 18, and 20. At day 21, the mice were injected intra-tracheally with 50 µg Der p and sacrificed 3 days later (Day 24).

AHR and the total cells infiltrated into the BALFs were examined as described above. A lower level of airway resistant was observed in the group (ii) and group (iv) mice, as compared with the group (i) and group (iii) mice. Further, the cell numbers in the BALFs from the group (iii) and group (iv) mice were lower than those in the BALFs from the group (i) and group (ii) mice.

Figure 3:
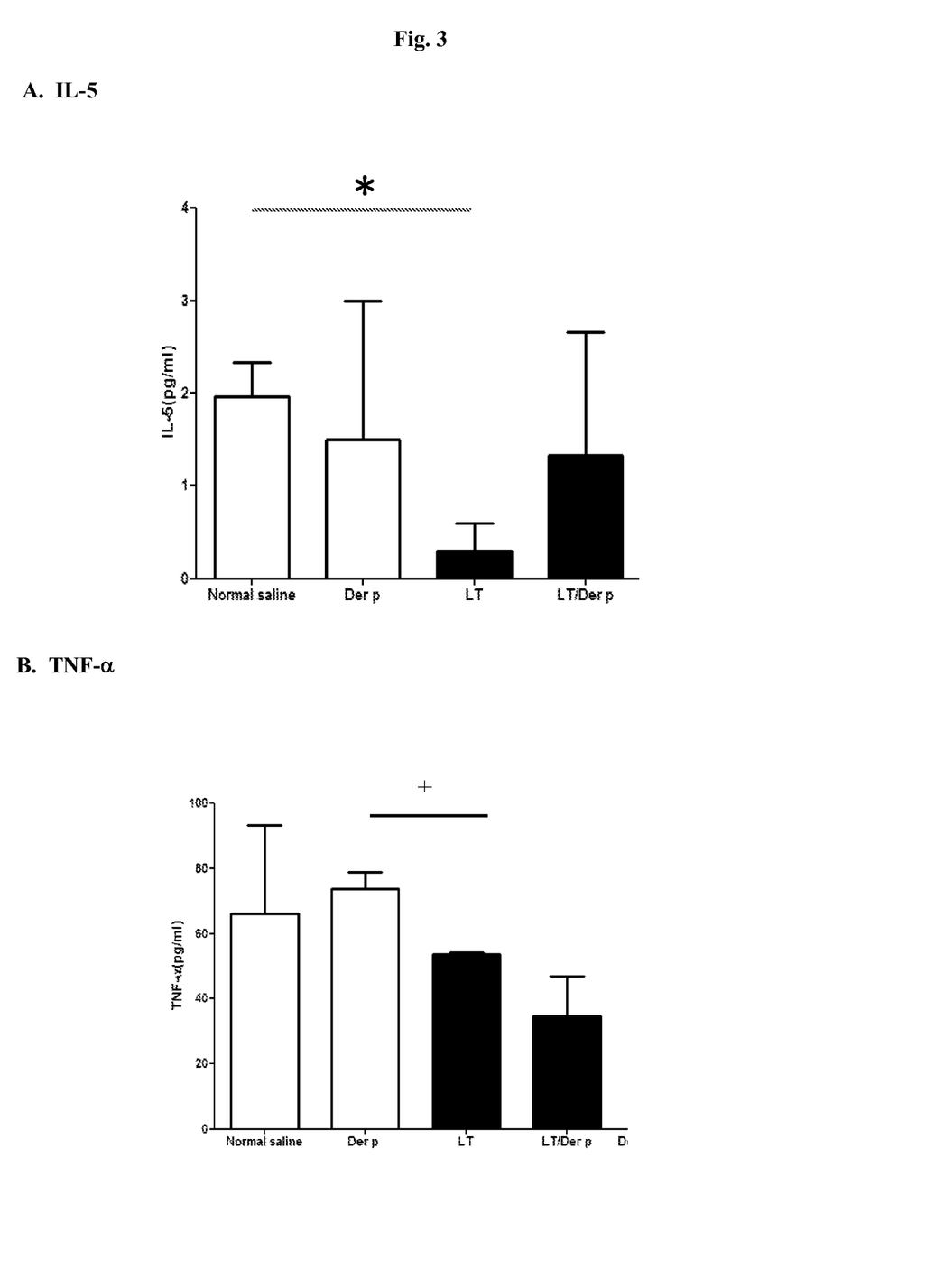
FIG. 3 is a diagram showing the levels of certain cytokines (A: IL-5; B: TNF-α; C: IL-12; D: Eotaxin; and E: thymus and activation-regulated chemokine (TARC) in Bronchoalveolar lavage (BAL) fluids of the mice treated with LTS61K, Der p, or a combination thereof (LTS61K/Der p) following the therapeutic protocol shown in FIG. 1. $p<0.05$ (LTS61K versus control or LTS61K/Der p versus normal saline). +: $p<0.05$ (LTS61K versus Der p alone or LTS61K/Der p versus Der p alone). ++: $p<0.01$ (LTS61K versus Der p alone or LTS61K/Der p versus Der p alone). The p values were obtained by Student t-test. LT represents LTS61K.

The levels of various cytokines in the BALFs were determined by sandwich ELISA as described above. The cytokines levels, particularly Th2-type cytokines IL-5, TARC, and eotaxin, were significantly lower in the BALFs from the group (iii) and group (iv) mice, treated with LTS61K and its combination with Der p, respectively, than in the BALFs from the group (i) and group (ii) mice, treated with saline and Der p, respectively. See FIG. 3.

Splenocytes were isolated from the treated mice; their proliferation and cytokine production were determined as described above. No significant difference in splenocyte proliferation was observed in all of the four groups of mice. On the other hand, the levels of IFN-γ, IL-4, and IL-10 were significantly lower in the group (iii) and group (iv) mice, as relative to those in the group (i) and group (ii) mice.

Figure 1:
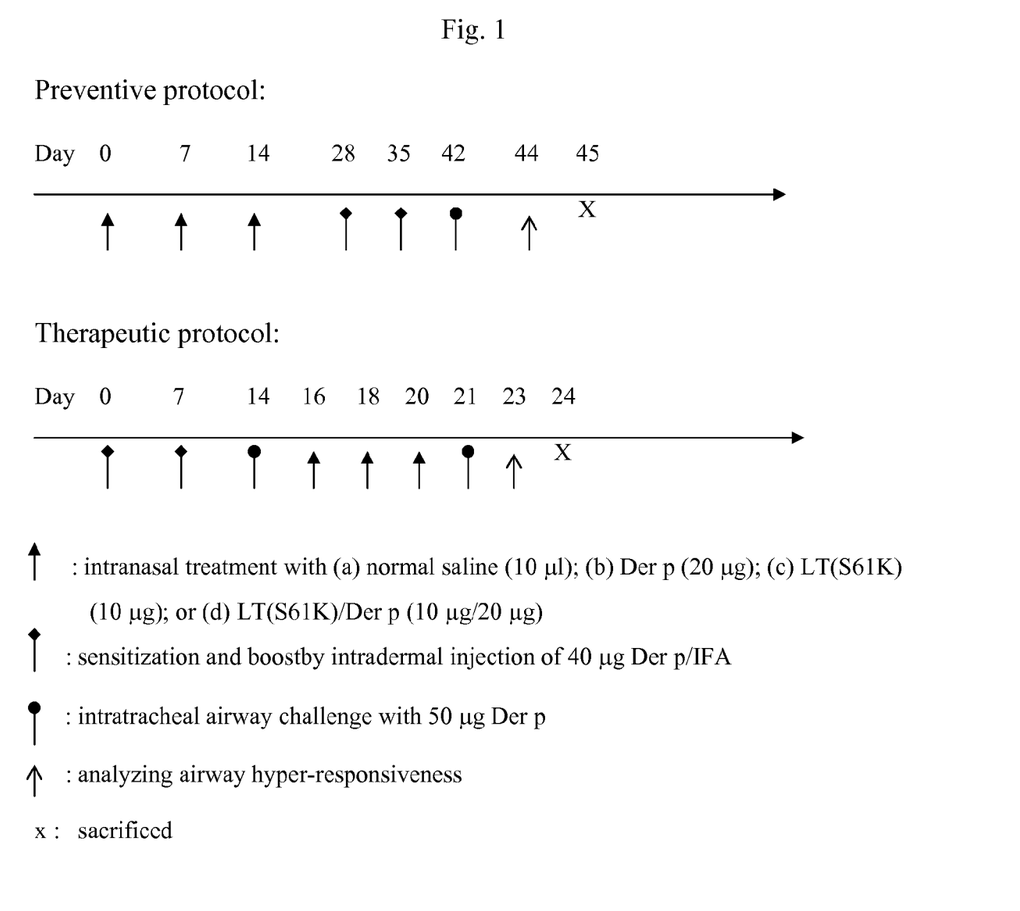
FIG. 1 is a diagram showing a preventive protocol and a therapeutic protocol for treating asthma mice with LT mutant LTS61K, allergen Dermatophagoides pteronyssinus (Der p), or a combination thereof.

In sum, the results discussed above show that LTS61K, either alone or in combination with Der p, suppressed TARC and Th2-type immune response when administered to asthma mice following the therapeutic protocol shown in FIG. 1.

Example 2

Figure 4:
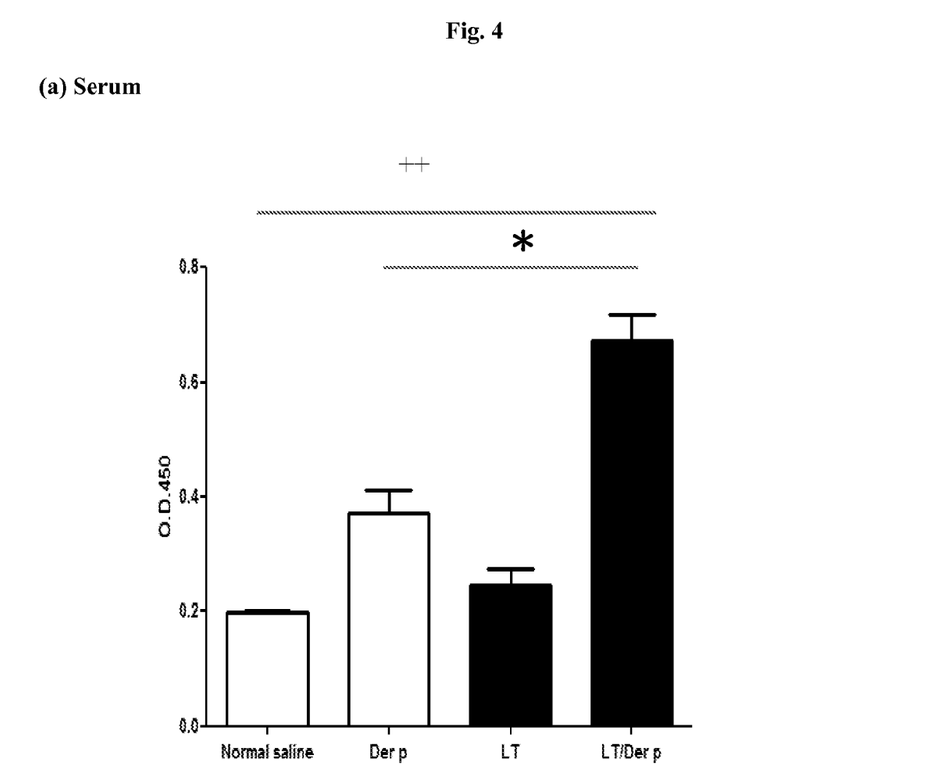
FIG. 4 is a diagram showing serum (panel a) and BAL fluid (panel b) levels of Der p-specific IgA in the mice treated with LTS61K, Der p, or a combination thereof (LTS61K/Der p) following the preventive protocol shown in FIG. 1. *: $p<0.05$ (LTS61K/Der p versus Der p alone). ++: $p<0.01$ (LTS61K/Der versus normal saline). The p values were obtained by Student t-test. LT represents LTS61K.
Figure 5:
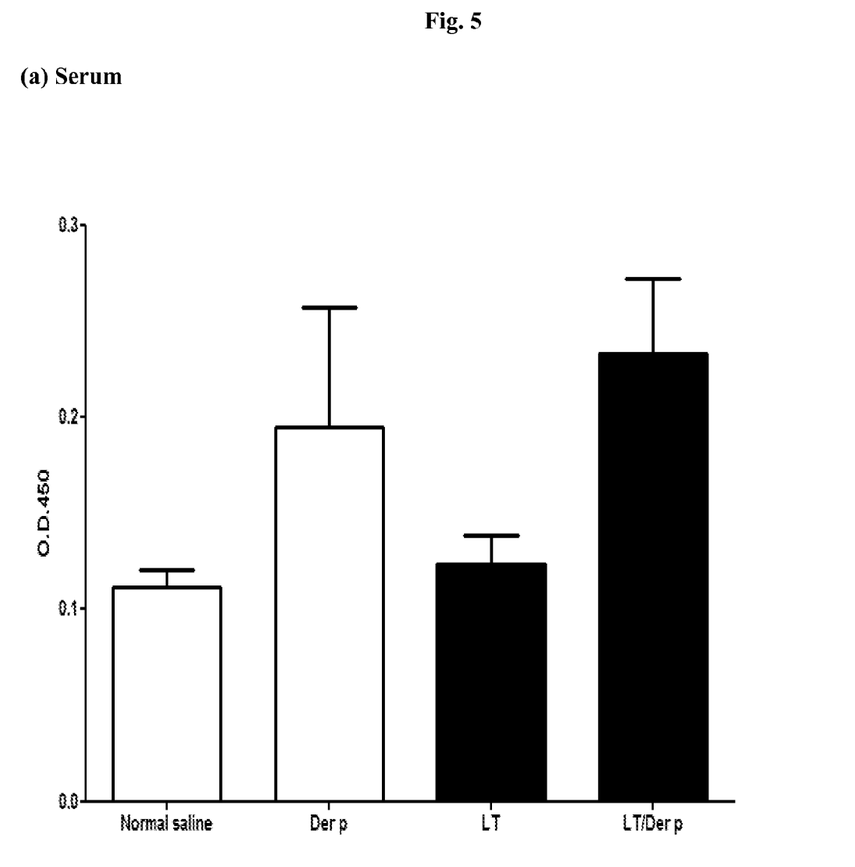
FIG. 5 is a diagram showing serum (panel a) and BAL fluid (panel b) levels of Der p-specific IgA in the mice treated with LTS61K, Der p, or a combination thereof (LTS61K/Der p) following the therapeutic protocol shown in FIG. 1. *: $p<0.05$ (LTS61K/Der p versus Der p alone). +: $p<0.05$ (LTS61K/Der p versus normal saline). The p values were obtained by Student t-test. LT represents LTS61K.

Local and Systemic Induction of Allergen-Specific IgA in Asthma Mice by Intranasal Treatment of LTS61K Alone or in Combination with Der p Allergen-specific IgA has been reported to play a protective role in allergic asthma. The levels of Der p-specific IgA were examined in both the mice subjected to the preventive protocol and the mice subjected to the therapeutic protocol (see FIG. 1) as follows. A multi-well plate was coated with Der p (10 µg/well) in a coating buffer (15 mM $Na_2CO_3$ and 35 mM $NaHCO_3$, pH=9.6) at 4° C. overnight and then wash by PBST (0.05% Tween 20 in PBS) and blocked by 0.5% BSA (Sigma-Aldrich). Serum or BAL fluid samples from the mice were diluted and incubated in the coated plate at 4° C. overnight. HRP-conjugated goat anti-mouse IgA antibodies (1:10000, Novus Biologicals) were then added to the plate. After the plate was washed by PBST, tetramethylbenzidine (TMB, Clinical Science Products) was added therein for signal development. As shown in FIGS. 4 and 5, the combination of LTS61K and Der p induced anti-Der p IgA production in both blood and BALFs in mice treated following either the preventive or therapeutic protocol.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for treating allergy, comprising administering to a subject in need thereof a composition containing a detoxified *E. coli* heat-labile enterotoxin (LT) in an amount effective for inducing an anti-allergic response in the subject, wherein the detoxified LT contains a wild-type subunit B and a mutated subunit A having the amino acid sequence of SEQ ID NO: 1 with a single mutation, the mutation being K at the position corresponding to position 61 in SEQ ID NO:1.

2. The method of claim 1, wherein the subject suffers from or is at risk for asthma.

3. The method of claim 1, wherein the composition is administered mucosally or transcutaneously.

4. The method of claim 3, wherein the composition is administered intranasally, or sublingually.

5. The method of claim 1, wherein the composition is in a pharmaceutical composition that is free of allergens.

6. The method of claim 5, wherein the subject suffers from or is at risk for asthma.

7. The method of claim 5, wherein the pharmaceutical composition is administered mucosally or transcutaneously.

8. The method of claim 7, wherein the pharmaceutical composition is administered intranasally or sublingually.

9. The method of claim 1, wherein the composition is a pharmaceutical composition that contains an allergen to which the subject is allergic.

10. The method of claim 9, wherein the subject suffers from or is at risk for asthma.

11. The method of claim 9, wherein the pharmaceutical composition is administered mucosally or transcutaneously.

12. The method of claim 11, wherein the pharmaceutical composition is administered intranasally or sublingually.

* * * * *

SEQUENCE LISTING

```
<160> NUMBER OF SEQ ID NOS: 3

<210> SEQ ID NO 1
<211> LENGTH: 240
<212> TYPE: PRT
<213> ORGANISM: Escherichia coli

<400> SEQUENCE: 1

Asn Gly Asp Lys Leu Tyr Arg Ala Asp Ser Arg Pro Pro Asp Glu Ile
1               5                   10                  15

Lys Arg Ser Gly Gly Leu Met Pro Arg Gly His Asn Glu Tyr Phe Asp
            20                  25                  30

Arg Gly Thr Gln Met Asn Ile Asn Leu Tyr Asp His Ala Arg Gly Thr
        35                  40                  45

Gln Thr Gly Phe Val Arg Tyr Asp Asp Gly Tyr Val Ser Thr Ser Leu
    50                  55                  60

Ser Leu Arg Ser Ala His Leu Ala Gly Gln Ser Ile Leu Ser Gly Tyr
65                  70                  75                  80

Ser Thr Tyr Tyr Ile Tyr Val Ile Ala Thr Ala Pro Asn Met Phe Asn
                85                  90                  95

Val Asn Asp Val Leu Gly Val Tyr Ser Pro His Pro Tyr Glu Gln Glu
            100                 105                 110

Val Ser Ala Leu Gly Gly Ile Pro Tyr Ser Gln Ile Tyr Gly Trp Tyr
        115                 120                 125

Arg Val Asn Phe Gly Val Ile Asp Glu Arg Leu His Arg Asn Arg Glu
    130                 135                 140

Tyr Arg Asp Arg Tyr Tyr Arg Asn Leu Asn Ile Ala Pro Ala Glu Asp
145                 150                 155                 160

Gly Tyr Arg Leu Ala Gly Phe Pro Pro Asp His Gln Ala Trp Arg Glu
                165                 170                 175

Glu Pro Trp Ile His His Ala Pro Gln Gly Cys Gly Asn Ser Ser Arg
            180                 185                 190

Thr Ile Thr Gly Asp Thr Cys Asn Glu Glu Thr Gln Asn Leu Ser Thr
        195                 200                 205

Ile Tyr Leu Arg Lys Tyr Gln Ser Lys Val Lys Arg Gln Ile Phe Ser
    210                 215                 220

Asp Tyr Gln Ser Glu Val Asp Ile Tyr Asn Arg Ile Arg Asn Glu Leu
225                 230                 235                 240

<210> SEQ ID NO 2
<211> LENGTH: 124
<212> TYPE: PRT
<213> ORGANISM: Escherichia coli

<400> SEQUENCE: 2

Met Asn Lys Val Lys Cys Tyr Val Leu Phe Thr Ala Leu Leu Ser Ser
```

```
  1               5                 10                15
Leu Cys Ala Tyr Gly Ala Pro Gln Ser Ile Thr Glu Leu Cys Ser Glu
            20                  25                30

Tyr Arg Asn Thr Gln Ile Tyr Thr Ile Asn Asp Lys Ile Leu Ser Tyr
            35                  40                45

Thr Glu Ser Met Ala Gly Lys Arg Glu Met Val Ile Ile Thr Phe Lys
        50                  55                60

Ser Gly Ala Thr Phe Gln Val Glu Val Pro Gly Ser Gln His Ile Asp
 65                 70                  75                80

Ser Gln Lys Lys Ala Ile Glu Arg Met Lys Asp Thr Leu Arg Ile Thr
                85                  90                95

Tyr Leu Thr Glu Thr Lys Ile Asp Lys Leu Cys Val Trp Asn Asn Lys
             100                 105               110

Thr Pro Asn Ser Ile Ala Ala Ile Ser Met Glu Asn
             115                 120

<210> SEQ ID NO 3
<211> LENGTH: 1148
<212> TYPE: DNA
<213> ORGANISM: Escherichia coli

<400> SEQUENCE: 3
atgaaaaata taactttcat tttttttatt ttattagcat cgccattata tgcaaatggc    60
gacaaattat accgtgctga ctctagaccc ccagatgaaa taaaacgttc cggaggtctt   120
atgcccagag gcataatga gtacttcgat agaggaactc aaatgaatat taatctttat   180
gatcacgcga gaggaacaca aaccggcttt gtcagatatg atgacggata tgtttccact   240
tctcttagtt tgagaagtgc tcacttagca ggacagtcta tattatcagg atattccact   300
tactatatat atgttatagc gacagcacca aatatgttta atgttaatga tgtattaggc   360
gtatacagcc ctcacccata tgaacaggag gtttctgcgt taggtggaat accatattct   420
cagatatatg gatggtatcg tgttaattt ggtgtgattg atgaacgatt acatcgtaac   480
agggaatata gagaccggta ttacagaaat ctgaatatag ctccggcaga ggatggttac   540
agattagcag gtttcccacc ggatcaccaa gcttggagag aagaaccctg gattcatcat   600
gcaccacaag gttgtggaaa ttcatcaaga caattacag gtgatacttg taatgaggag   660
acccagaatc tgagcacaat atatctcagg aaatatcaat caaaagttaa gaggcagata   720
ttttcagact atcagtcaga ggttgacata tataacagaa ttcggaatga attatgaata   780
aagtaaaatg ttatgtttta tttacggcgt tactatcctc tctatgtgca tacggagctc   840
cccagtctat tacagaacta tgttcggaat atcgcaacac acaaatatat acgataaatg   900
acaagatact atcatatacg gaatcgatgg caggcaaaag agaaatggtt atcattacat   960
ttaagagcgg cgcaacattt caggtcgaag tcccgggcag tcaacatata gactcccaaa  1020
aaaaagccat tgaaaggatg aaggacacat taagaatcac atatctgacc gagaccaaaa  1080
ttgataaatt atgtgtatgg aataataaaa cccccaattc aattgcggca atcagtatgg  1140
aaaactag                                                           1148
```